United States Patent
Boira Bonhora et al.

(10) Patent No.: US 11,179,485 B2
(45) Date of Patent: Nov. 23, 2021

(54) DEVICE FOR STERILIZATION OF FLEXIBLE BAGS AND METHOD FOR STERILIZING FLEXIBLE BAGS

(71) Applicant: GRIFOLS ENGINEERING, S.A., Parets del Valles (ES)

(72) Inventors: Jordi Boira Bonhora, Terrassa (ES); Daniel Fleta Coit, Bigues (ES); Carlos Roura Salietti, Arenys de Munt (ES)

(73) Assignee: GRIFOLS ENGINEERING, S.A., Parets del Valles (ES)

( * ) Notice: Subject to any disclaimer, the term of this patent is extended or adjusted under 35 U.S.C. 154(b) by 126 days.

(21) Appl. No.: 16/326,167

(22) PCT Filed: May 31, 2017

(86) PCT No.: PCT/ES2017/070386
§ 371 (c)(1),
(2) Date: Feb. 15, 2019

(87) PCT Pub. No.: WO2018/167334
PCT Pub. Date: Sep. 20, 2018

(65) Prior Publication Data
US 2020/0000948 A1    Jan. 2, 2020

(30) Foreign Application Priority Data
Mar. 15, 2017   (ES) .................. ES201730338

(51) Int. Cl.
*A61L 2/08*   (2006.01)
*A61J 1/10*   (2006.01)
(Continued)

(52) U.S. Cl.
CPC .............. *A61L 2/087* (2013.01); *A61J 1/10* (2013.01); *A61L 2/26* (2013.01); *B65B 3/003* (2013.01);
(Continued)

(58) Field of Classification Search
None
See application file for complete search history.

(56) References Cited

U.S. PATENT DOCUMENTS 7,057,189 B2 * 6/2006 Coogan ............... A61M 1/3681
250/432 R
8,795,599 B2   8/2014 Fontcuberta
(Continued)

FOREIGN PATENT DOCUMENTS

CL    201703501    4/2018
CN    1720875 A    1/2006
(Continued)

OTHER PUBLICATIONS

Office Action and Patent Search Report, dated Sep. 19, 2018, received from the Patent Office of Taiwan in the corresponding Taiwanese Patent Application No. 106120367.
(Continued)

*Primary Examiner* — Hemant Desai
*Assistant Examiner* — Tanzim Imam
(74) *Attorney, Agent, or Firm* — Knobbe, Martens, Olson & Bear, LLP

(57) ABSTRACT

A device is for sterilization by electron beam irradiation of flexible bags, in particular flexible bags of the type that can contain solutions of human plasma proteins for therapeutic use. A sterilization method includes irradiating flexible bags by electron beam irradiation. An in-line method for filling flexible can use the sterilization device and method.

16 Claims, 3 Drawing Sheets

(51) Int. Cl.
  *A61L 2/26*  (2006.01)
  *B65B 3/00*  (2006.01)
  *B65B 55/08*  (2006.01)

(52) U.S. Cl.
  CPC ........... *B65B 55/08* (2013.01); *A61L 2202/11* (2013.01); *A61L 2202/181* (2013.01); *A61L 2202/23* (2013.01)

(56) References Cited

U.S. PATENT DOCUMENTS

| | | |
|---|---|---|
| 9,782,502 B2 | 10/2017 | Laguzzi |
| 2004/0086421 A1 | 5/2004 | Moller |
| 2005/0079096 A1* | 4/2005 | Brown-Skrobot ........ A61L 2/10 422/24 |
| 2006/0110282 A1 | 5/2006 | Bilstad |
| 2006/0153329 A1 | 7/2006 | Elyash et al. |
| 2008/0251156 A1 | 10/2008 | Kang et al. |
| 2009/0274576 A1* | 11/2009 | Ressler ..................... A23L 3/28 422/24 |
| 2010/0007492 A1* | 1/2010 | Ressler ..................... A61L 2/24 340/540 |
| 2011/0012032 A1 | 1/2011 | Bufano |
| 2014/0037498 A1* | 2/2014 | Laguzzi ................. A61L 2/087 422/22 |
| 2015/0069270 A1* | 3/2015 | Shur ........................ A23L 3/28 250/492.1 |
| 2015/0343235 A1* | 12/2015 | Blanche ............... A61N 5/0624 607/91 |
| 2017/0136135 A1 | 5/2017 | Feuilloley |
| 2017/0245616 A1* | 8/2017 | Lakios ..................... A61L 2/088 |
| 2019/0070323 A1* | 3/2019 | Atreya .................... A61L 2/084 |

FOREIGN PATENT DOCUMENTS

| | | |
|---|---|---|
| CN | 1289149 C | 12/2006 |
| CN | 103596596 A | 2/2014 |
| CN | 106456812 A | 2/2017 |
| EP | 1 834 655 A1 | 9/2007 |
| EP | 1 991 279 B1 | 4/2011 |
| EP | 2 854 138 A1 | 4/2015 |
| EP | 1 834 655 B1 | 3/2016 |
| EP | 2 854 138 B1 | 7/2017 |
| RU | 2295976 C2 | 3/2007 |
| RU | 2413536 C2 | 3/2011 |
| WO | WO 1997/042897 A1 | 11/1997 |
| WO | WO 2005/065623 A2 | 7/2005 |
| WO | WO 2013/130636 A2 | 9/2013 |
| WO | WO 2016/079032 A1 | 5/2016 |
| WO | WO 2017/001947 A1 | 1/2017 |

OTHER PUBLICATIONS

Expert and Search Report, dated Nov. 13, 2019, received from the Patent Office of Chile in the corresponding Chilean Patent Application No. 2019-00436.
International Search Report, dated Mar. 29, 2018, in International Patent Application No. PCT/ES2017/070386.
Office Action dated Aug. 3, 2020 in Chinese Application No. 201780051360.6.
Acceptance Decision dated Oct. 28, 2020 in Russian Application No. 2019104493/04(008514).
Search Report dated Aug. 4, 2020 in Russian Application No. 2019104493/04.
Written Opinion dated Dec. 8, 2020 in Singaporean Application No. 11201901375R.

* cited by examiner

DEVICE FOR STERILIZATION OF FLEXIBLE BAGS AND METHOD FOR STERILIZING FLEXIBLE BAGS

PRIORITY AND CROSS REFERENCE TO RELATED APPLICATIONS

This application is the U.S. National Phase Application under 35 U.S.C. § 371 of International Application No. PCT/ES2017/070386, filed May 31, 2017, designating the U.S. and published as WO 2018/167334 A1 on Sep. 20, 2018, which claims the benefit of Spanish Application No. ES P201730338, filed Mar. 15, 2017. Any and all applications for which a foreign or a domestic priority is claimed is/are identified in the Application Data Sheet filed herewith and is/are hereby incorporated by reference in their entireties under 37 C.F.R. § 1.57.

FIELD

The present invention relates to device and method for sterilizing flexible bags.

SUMMARY

The present invention relates to the pharmaceutical sector, specifically to a device for sterilization by electron beam irradiation of flexible bags, in particular flexible bags of the type that can contain solutions of human plasma proteins for therapeutic use. Furthermore, the present invention relates to a method of sterilization by electron beam irradiation of said flexible bags and to an in-line method for filling flexible bags that uses the sterilization device and method of the present invention.

BRIEF DESCRIPTION OF THE DRAWINGS

The invention will be explained below with reference to the figures, in which.

DETAILED DESCRIPTION

Electron beam irradiation, also abbreviated to "E-beam", is a form of ionising energy generally characterised by its low penetration and high doses of energy applied. Said beam is a stream of concentrated, highly charged electrons. The electrons are generated by an accelerator capable of producing beams that can be continuous or pulsed. The material to be sterilized absorbs the energy of the electrons and said energy absorption, also known as absorbed dose, eliminates any micro-organisms, destroying their DNA strands.

Commercial electron beam accelerator equipment usually operates with a single energy and, in the case of sterilization of pharmaceutical products, a high-energy electron beam is usually required to successfully penetrate the product and its packaging. A higher-energy electron beam will lead to greater penetration by said electron beam into the product.

When the electron beam is assessed with a view to carrying out sterilization, account has to be taken of various parameters such as the density, size and orientation of the product, and the packaging. E-beam irradiation generally works better when used for low-density products, packed uniformly.

In the particular case of flexible bags suitable for containing a solution of human plasma proteins, these are formed from various materials in various thicknesses. For example, the walls of the bag can be approximately 130 µm thick, the tube of the outlet port of the bag, which is sealed to the latter, can be 1.24 mm thick, whilst the twist-off cap is the zone of greatest thickness, which can be approximately 3 mm. All these portions have to be decontaminated and sterilized before the bags are filled with said human plasma protein solutions.

The electron beam energy needed to carry out sterilization of said flexible bags is therefore different for each of the portions mentioned, being lowest for the walls of the bag and greatest for the outlet port tube and the cap. A conventional electron beam accelerator, which emits a single energy, may not be suitable for these cases, given that the energy would be higher than necessary to perform the sterilization for some portions of the bag or insufficient for others.

The authors of the present invention have developed an electron beam sterilization device that allows sterilization of this type of bags and a sterilization method for said bags without the need to apply high energies, since the energy necessary for sterilization will be applied to each portion according to the characteristics of said portion, specifically its thickness.

Figure 1:
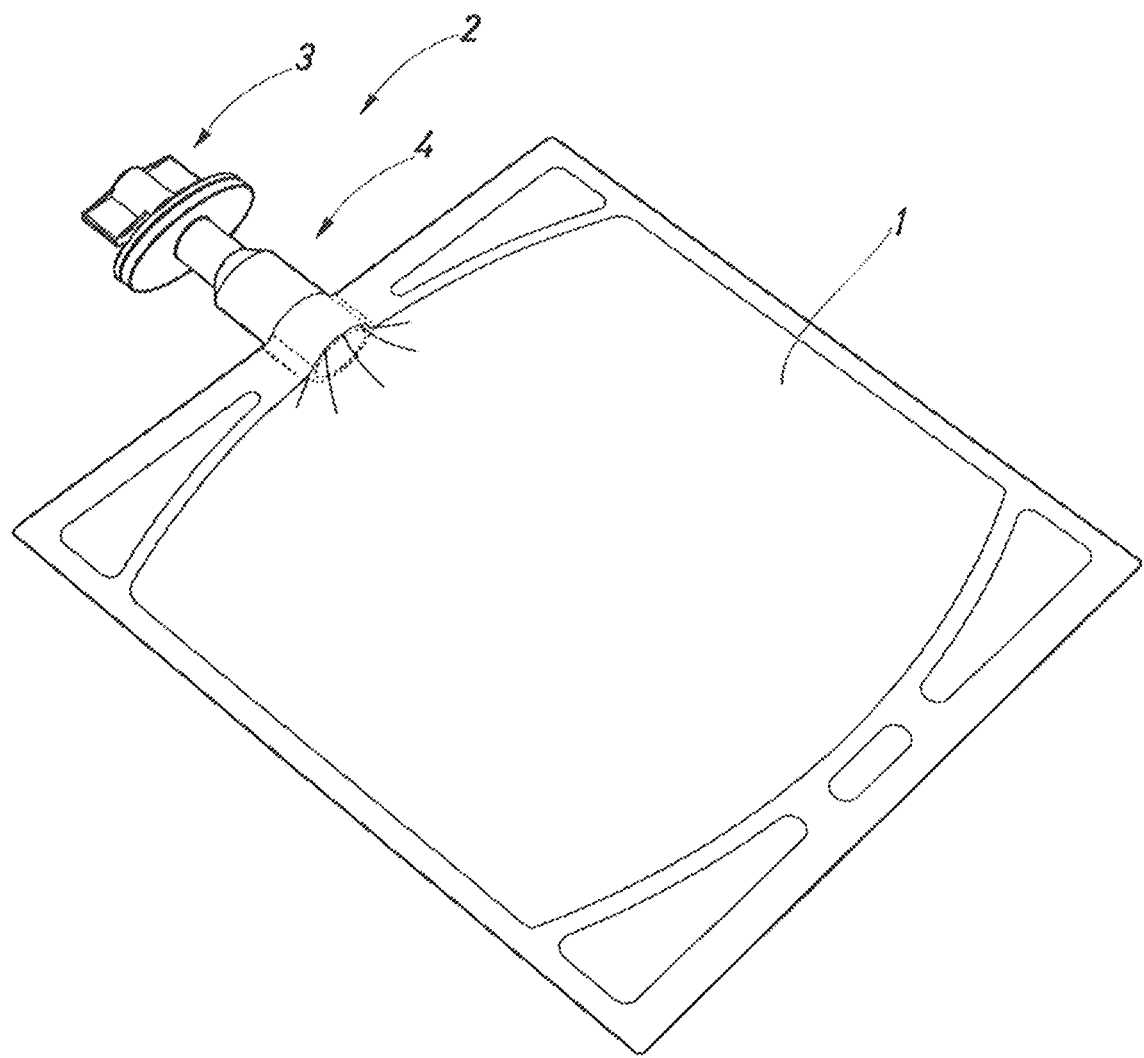
FIG. 1 is a perspective view of an empty flexible bag suitable for containing human plasma proteins.

An example of the flexible bags to be sterilized using the sterilization device of the present invention is shown in FIG. 1. Said bags can have a volume of 50 mL to 500 mL. FIG. 1 shows an empty bag —2— that contains a port/cap structure. The walls —1— of said bag can be approximately 130 µm thick, the tube of the outlet port —4— of the bag can be approximately 1.24 mm thick, whilst the twist-off cap —3— can have a thickness of approximately 3 mm.

In a first aspect, the present invention relates to a device for sterilizing flexible bags, characterised in that it comprises a sterilization zone formed by at least two electron accelerators that emit electron beams at different energies.

In a first embodiment, said sterilisation device comprises at least one accelerator that emits an electron beam at an energy of between 450-500 keV and at least one other accelerator that emits an electron beam at an energy of 700-750 keV. Preferably, said sterilisation device has one accelerator that emits an electron beam at an energy of between 450-500 keV and another accelerator that emits an electron beam at an energy of 700-750 keV.

Figure 2:
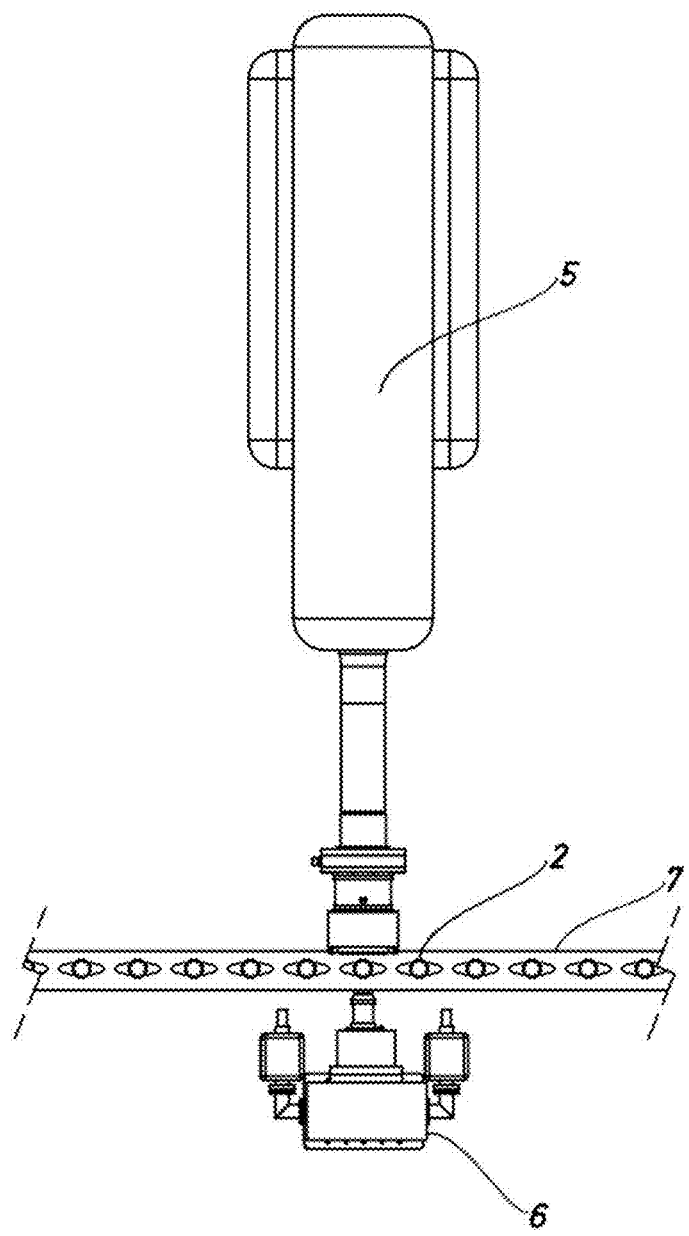
FIG. 2 is a view from above of the sterilization zone of one embodiment of the electron beam sterilization device according to the present invention.

FIG. 2 is a view from above of the sterilisation zone of one embodiment of the sterilisation device according to the present invention. Said sterilisation zone is formed by a lower-energy electron beam accelerator or emitter —5— (450-500 keV), a higher-energy electron beam accelerator or emitter —6— (700-750 keV) and a zone —7— in which the flexible bags to be sterilised are placed. In this embodiment, the two accelerators are positioned on opposite sides of the bags in a position facing each other.

Figure 3:
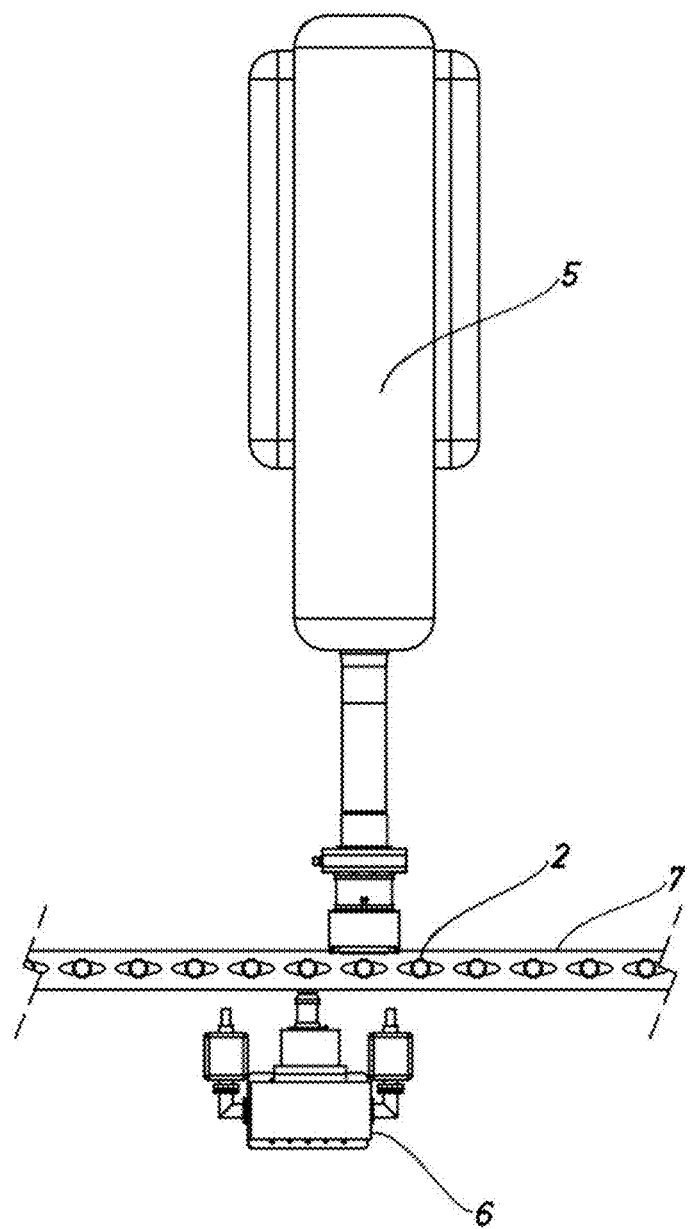
FIG. 3 is a view from above of the sterilization zone of another embodiment of the electron beam sterilization device according to the present invention.

FIG. 3 is a view from above of the sterilisation zone of another embodiment of the sterilisation device according to the present invention. Said sterilisation zone is formed by a lower-energy electron beam accelerator or emitter —5— (450-500 keV), a higher-energy electron beam accelerator or emitter —6— (700-750 keV) and a zone —7— in which the flexible bags to be sterilised are placed. In this embodiment, the two accelerators are positioned on opposite sides of the bags in a position in which they do not face each other.

In another aspect, the present invention discloses a method for sterilising flexible bags containing a solution of human plasma proteins, using the above-mentioned electron beam accelerator device. Said method is characterised in that it comprises the following steps:

a) at least one emission of an electron beam at an energy of 450-500 keV;

b) after a period of approximately 10 ns emission of a second electron beam at an energy of 700-750 keV.

A person skilled in the art will understand that the higher-energy electron beam is aimed at the zone of the bag of greatest thickness, i.e. at the tube of the outlet port and the cap, whereas the lower-energy electron beam is aimed at the walls of the bag.

In one embodiment of the electron beam accelerator device of the present invention, the distance from the flexible bag to be sterilised to the irradiation source is between 1.5 cm and 2.5 cm. Preferably, said distance is 2 cm.

The sterilization method of the present invention can be carried out before or after filling the bag and is preferably performed in a sterile environment.

The flexible bag to be sterilized by the method of the present invention can be made from any of the materials that are appropriate for the pharmaceutical industry and known in the state of the art.

Furthermore, said flexible bag can contain pharmaceutical solutions of biological origin, such as blood or blood products such as plasma, serum, red blood cells, albumin, α1-antitrypsin, von Willebrand factor, coagulation factors such as factor VII, factor VIII and factor IX, immunoglobulins, plasminogen, plasmin, antithrombin III, fibrinogen, fibrin, thrombin or combinations thereof. It is also provided for the pharmaceutical liquid or product to be of non-biological origin, and obtained by any other process or method known in the state of the art, for example, chemical synthesis, recombinant production or transgenic production.

In a final aspect, the present invention relates to an in-line method for filling flexible bags with human plasma proteins, which comprises a step of electron beam sterilization using a device as mentioned above.

Said in-line method for filling flexible bags comprises the steps of:

a) labelling the bags;

b) sterilizing the bags by electron beam;

c) filling the bags with the solution of human plasma proteins in a sterile environment; and d) sealing the bags.

The flexible bags that can be sterilized by the method of the present invention can have a volume of 50 mL to 500 mL. FIG. 1 is a perspective view.

Furthermore, said flexible bag can contain pharmaceutical solutions of biological origin, such as blood or blood products such as plasma, serum, red blood cells, albumin, α1-antitrypsin, von Willebrand factor, coagulation factors such as factor VII, factor VIII and factor IX, immunoglobulins, plasminogen, plasmin, antithrombin III, fibrinogen, fibrin, thrombin or combinations thereof. It is also provided for the pharmaceutical liquid or product to be of non-biological origin, and obtained by any other process or method known in the state of the art, for example, chemical synthesis, recombinant production or transgenic production.

To aid understanding, the present invention is described below with reference to the following example, which in no way purports to restrict the present invention.

Example. Determination of the Electron Beam Energy Needed for Each Portion of the Flexible Bag Bags having four different volumes (50, 100, 250 and 500 mL), produced by Grifols S. A., were tested. However, the thicknesses of all the bags are the same in all four formats, the characteristics of which are summarised in Table 1 below. The walls of the bags are formed by a film of multiple layers bonded together by a layer of adhesive.

TABLE 1

Characteristics of the walls of the flexible bags.

| Bag | Layer 1 (PET-SiO) | Layer 2 (OPA) | Layer 3 (PP-SiO) | Layer 4 (PP) |
|---|---|---|---|---|
| Formula | $C_{10}H_8O_4SiO$ | $C_8H_6O_2$ | $C_3H_6SiO$ | $C_3H_6$ |
| Density (g/cm$^3$) | 1.42 | 1.13 | 0.889 | 0.894 |
| Thickness (μm) | 12 | 15 | 18 | 85 |

The total thickness of the bag wall is 130 μm, without taking into account the intermediate layers of adhesive, which can be ±12 μm thick. On the other hand, on measurement, the total thickness of the cap was found to be 2.85 mm.

For this study, four electron beam energies were chosen: 250 keV with a current of 5.5 kA, 450 keV with a current of 8.5 kA, 650 keV with 12.5 kA and 850 with 16 kA. The distance from the irradiation window was 2 cm.

At the 250-keV energy, approximately half the electrons were stopped by the bag wall, producing a lower flux ($3.5 \times 10^3$ electrons/cm$^2$). However, at an energy of 450 keV, sufficient energy was produced to treat the inner portion of the bag, even bonding the two walls of the bag having a thickness of 260 μm.

The electron beams of 250 keV and 450 keV were not penetrative enough to pass through the tube of the outlet port of the bag. On the other hand, a large difference between the 650-keV and 850-keV beams was found with respect to the dose deposited (approximately 30 times), and therefore a study of two intermediate energies of 700 keV and 750 keV was conducted. It has been observed that, at the 700-keV energy, the electrons are able to pass through the inner tube of the cap, which is 2.85 mm thick, and at 750 keV a deposited dose that is 10 times higher is produced.

What is claimed is:

1. A device for sterilizing flexible bags, the device comprising a sterilization zone comprising at least two electron accelerators that are configured to emit electron beams at different energies, wherein the at least two electron accelerators comprise a first accelerator configured to emit an electron beam at an energy of 450-500 keV and a second accelerator configured to emit an electron beam at an energy of 700-750 keV.

2. The device according to claim 1, wherein the at least two electron accelerators are positioned on opposite sides of the bags in a position in which they face each other.

3. The device according to claim 1, wherein the at least two electron accelerators are positioned on opposite sides of the bags in a position in which they do not face each other.

4. A method for sterilizing flexible bags containing solutions of human plasma proteins by electron beams emitted from the device according to claim 1, the method comprising:

exposing the flexible bags to a first electron beam emitted from the first accelerator at an energy of 450-500 keV;

after a period of 10 ns after exposing the flexible bags to the first electron beam, exposing the flexible bags to at least one second electron beam emitted from the second accelerator at an energy of 700-750 keV, thereby sterilizing the flexible bags.

5. The method according to claim 4, wherein a distance between the flexible bags to be sterilized and the first accelerator or the second accelerator is between 1.5 cm and 2.5 cm.

6. The method according to claim 5, wherein the distance between the flexible bags to be sterilized and the first accelerator or the second accelerator is 2 cm.

7. The method according to claim 4, wherein the flexible bags to be sterilized have a capacity sufficient to contain solutions of 50 mL to 500 mL volume.

8. The method according to claim 4, wherein the solutions contained in the flexible bags are solutions of biological origin.

9. The method according to claim 4, wherein the solutions are obtained by chemical synthesis, recombinant production or transgenic production.

10. The method according to claim 8, wherein the solutions of biological origin are blood or blood products selected from the group consisting of plasma, serum, red blood cells, albumin, al-antitrypsin, von Willebrand factor, coagulation factors, immunoglobulins, plasminogen, plasmin, antithrombin III, fibrinogen, fibrin, thrombin, and combinations thereof.

11. The method according to claim 10, wherein the coagulation factors are selected from the group consisting of factor VII, factor VIII, and factor IX.

12. An in-line method for filling flexible bags, the method comprising:
labelling the bags;
sterilizing the flexible bags according to the method of claim 4;
filling the bags with solutions of biological origin in a sterile environment; and
sealing the bags.

13. The method according to claim 12, wherein the flexible bags to be sterilized are capable of containing solutions of 50 mL to 500 mL volume.

14. The method according to claim 12, wherein the solutions are obtained by chemical synthesis, recombinant production or transgenic production.

15. The method according to claim 12, wherein the solutions of biological origin are blood or blood products selected from the group consisting of plasma, serum, red blood cells, albumin, al-antitrypsin, von Willebrand factor, coagulation factors, immunoglobulins, plasminogen, plasmin, antithrombin III, fibrinogen, fibrin, thrombin, and combinations thereof.

16. The method according to claim 15, wherein the coagulation factors are selected from the group consisting of factor VII, factor VIII, and factor IX.

\* \* \* \* \*